United States Patent [19]

Cricchio et al.

[11] 4,002,754
[45] Jan. 11, 1977

[54] SUBSTITUTED PIPERAZINYLIMINORIFAMYCINS

[75] Inventors: Renato Cricchio, Varese; Vittorio Arioli, Como, both of Italy

[73] Assignee: Gruppo Lepetit, S.p.A., Milan, Italy

[22] Filed: Feb. 26, 1976

[21] Appl. No.: 661,586

[30] Foreign Application Priority Data

Mar. 5, 1975 United Kingdom ............... 9058/75

[52] U.S. Cl. .......................... 424/250; 260/239.3 P
[51] Int. Cl.² ..................................... C07D 491/08
[58] Field of Search ............. 260/239.3 P; 424/250

[56] References Cited

UNITED STATES PATENTS 3,342,810   9/1967   Maggi et al. ............... 260/239.3 P Primary Examiner—Natalie Trousof
Assistant Examiner—Robert T. Bond
Attorney, Agent, or Firm—Theodore Post; C. Kenneth Bjork

[57] ABSTRACT

Substituted piperazinyliminorifamycins having the following structural formula:

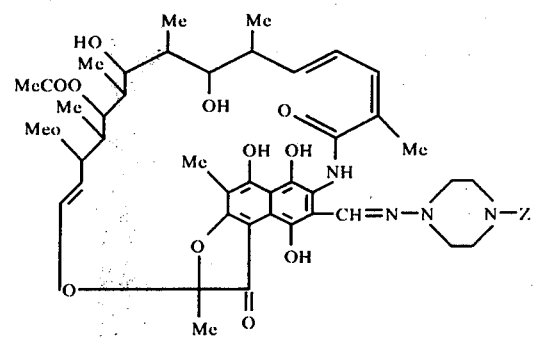

wherein Me represents a methyl group and Z represents alkenyl of 3 to 5 carbon atoms, alkynyl of 3 to 5 carbon atoms, 5- or 7-membered cycloalkenyl, cycloalkyl-($C_1$–$C_2$) alkyl wherein the cycloalkyl moiety is a 3- or 7-membered ring or cycloalkenyl-($C_1$–$C_2$)alkyl wherein the cycloalkenyl moiety is a 5- or 7-membered ring. The compounds have a broad spectrum antibacterial utility accompanied by a low toxicity.

9 Claims, No Drawings

SUBSTITUTED PIPERAZINYLIMINORIFAMYCINS

BACKGROUND OF THE INVENTION

Some condensation products of 3-formylrifamycin SV with aminopiperazines are described in U.S. Pat. No. 3,342,810. Among the compounds therein described, the condensation product of 4-methyl-1-aminopiperazine with 3-formylrifamycin SV (rifampicin) has found wide application in chemotherapy against infectious diseases and, particularly, against tuberculosis and leprosy.

In the prior literature there are reported no condensation products of 3-formylrifamycin SV with 1-aminopiperazines having an unsaturated aliphatic radical or a cycloaliphatic in the 4-position of the piperazine ring.

SUMMARY OF THE INVENTION

This invention relates to novel compounds of the rifamycin family characterized by the following structural formula:

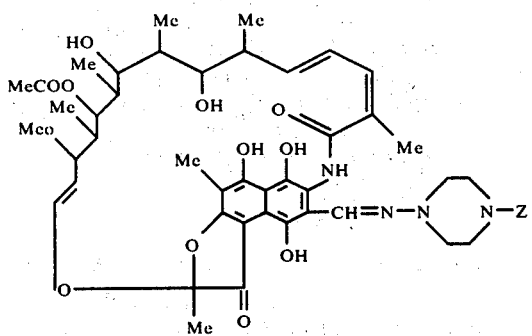

wherein Me represents a methyl group and Z represents alkenyl of 3 to 5 carbon atoms, 5- or 7-membered cycloalkenyl, cycloalkyl-($C_1$-$C_2$)alkyl wherein the cycloalkyl moiety is a 3- to 7-membered ring or cycloalkenyl-($C_1$-$C_2$)alkyl wherein the cycloalkenyl moiety is a 5- or 7-membered ring. The cycloalkyl and cycloalkenyl moieties may be unsubstituted or may have one or two $C_1$-$C_2$ alkyl groups as the substituents on the ring.

The compounds of the invention have a broad spectrum antibacterial utility accompanied by a low toxicity.

The new rifamycin products, besides possessing the usual broad spectrum of activity which is peculiar to this class of compounds, are characterized by the fact that they also have a remarkably long-lasting therapeutic effectiveness in treatments, with administration schedules allowing unusually large intervals of time between subsequent administrations. This lasting property offers considerable advantages in therapeutic practice, since it allows one to obtain good results without the need of daily administration. In some experiments carried out with the novel rifamycins on mammals such as mice, one or two administrations per week have shown the same or better effectiveness than a daily administration of the same dose level of rifampicin. The necessity of a frequent administration schedule, such as a daily administration, to obtain a reliable therapeutic effect, besides the disadvantage of taking a larger amount of biologically active substance during the whole therapy cycle, undoubtedly represents for the patient a troublesome task, in particular for long term, ambulatory therapy.

The unexpected biological characteristics of the novel rifamycins have been evidenced by considering the survival time after a daily administration of rifampicin and a once-a-week administration of the same dose level per os of 3-[4-(2-propenyl)-1-piperazinyl]iminorifamycin SV (hereinafter referred to as "propenyl derivative") to mice infected with *Mycobacterium tuberculosis* $H_{37}R_v$. The mice treated with propenyl derivative showed about the same survival time although each of them actually received a total amount of active substance which was about 1/6 of the total amount of the active substance received by each of the animals under the rifampicin regimen. The novel rifamycins, besides the above-mentioned lasting properties, possess a very good antimicrobial activity and a low toxicity. For instance, the value of the minimal inhibitory concentration of propenyl derivative against *Mycobacterium tuberculosis* $H_{37}R_v$ is 0.02 $\mu$g/ml while that of rifampicin is 0.5 $\mu$g/ml. The $LD_{50}$ of the propenyl derivative in mice is about 1500 mg/kg p.o. and about 700 mg/kg i.p., while the corresponding values for rifampicin are, respectively, 907 and 416.

The outstanding effectiveness and safety of the new rifamycins in combatting microbial infections has been proved also in experimental *Staphylococcus aureus* infections in mice. In fact, propynyl derivative (i.e. 3-[4-(2-propynyl)-1-piperazinyl]iminomethylrifamycin SV) in representative experiments has shown an $ED_{50}$ value of 0.20 mg/kg p.o. The toxicity is very low, the $LD_{50}$ value in mice being higher than 2000 mg/kg p.o. The new compounds are suitably administered in usual pharmaceutical combinations with conventional carriers.

DESCRIPTION OF SOME PREFERRED EMBODIMENTS

The following additional description and examples further describe the invention and the manner and process of making and using it to enable the art skilled to make and use the same and set forth the best mode contemplated by the inventors of carrying out the invention.

The novel rifamycins are prepared by condensing 3-formylrifamycin SV with an aminopiperazine of the formula

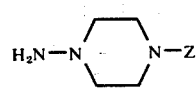

wherein Z has the meaning previously given. In the condensation, 3-formylrifamycin SV is contacted with a substantially equimolar proportion (preferably with a 0.1 molar excess) of the indicated aminopiperazine in the presence of an inert organic solvent such as, for instance, dioxane, tetrahydrofuran, methanol, ethanol, benzene or ethyl acetate. The temperature of the reaction ranges from ambient temperature to reflux temperature of the reaction mixture. The reaction is generally followed by thin layer chromatography. After the reaction is substantially complete, the solvent is distilled off under reduced pressure and the residue is purified by crystallization from a solvent or by column chromatography. Suitable solvents for crystallization are the lower alkanols, ethyl acetate, hexane or mixtures thereof.

The synthesis of the aminopiperazine reactant is accomplished by following known procedures which involve alkylation of N-nitroso piperazine with an appropriate agent of the formula Z-halo wherein "halo" stands for chloro or bromo and Z has the same meaning as before, followed by reduction of the nitroso group with LiAlH₄ to obtain the corresponding amino derivative. An alternative route for the aminopiperazine reactant consists in the nitrosation of a piperazine of the formula

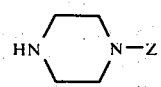

wherein Z has the same meaning as before, followed by reduction of the nitroso group with LiAlH₄.

Examples of compounds falling within the scope of the invention which are prepared according to the process are those of Formula I wherein the substituents at the piperazine nitrogen represented by Z have one of the following meanings:

2-propenyl, 2-butenyl, 3-butenyl, 1-methyl-2-propenyl, 2-methyl-2-propenyl, pentenyl, 3-pentenyl, 4-pentenyl, 2-methyl-2-butenyl, 1-methyl-2-butenyl, 3-methyl-2-butenyl, 1,2-dimethyl-2-pentenyl, 3-methyl-3-butenyl, 1-methyl-3-butenyl, 2-propynyl, 1-methyl-2-propynyl, 2-butynyl, 3-butynyl, 2-pentynyl, 3-pentynyl, 4-pentynyl, 1-methyl-2-butynyl, 1-methyl-3-butynyl, 2-cyclopentenyl, 3-ethyl-2-cyclopentenyl, 3-cyclopentenyl, 2-cyclohexenyl, 3-cyclohexenyl, 4-methyl-3-cyclohexenyl, 2-cycloheptenyl, 3-cycloheptenyl, cyclopropylmethyl, 2-cyclopropylethyl, cyclobutylmethyl, 2-cyclobutylethyl, cyclopentylmethyl, (3,3-dimethylcyclobutyl)methyl, 2-cyclopentylethyl, cyclohexylmethyl, 2-cyclohexylethyl, cycloheptylmethyl, 2-cycloheptylethyl, (1-cyclobutenyl)methyl, 2-(2-cyclopentenyl)ethyl, (3-cyclopentenyl)methyl, (1-cyclopentenyl)methyl, 2-(1-cyclopentenyl)-ethyl, (1-cyclohexenyl)methyl or (1-cycloheptenyl)methyl.

The following non-limitative examples further illustrate the invention.

EXAMPLE 1

3-[4-(2-Propenyl)-1-piperazinyl]iminomethylrifamycin SV

To a suspension of 7.27 g (0.01 m) of 3-formylrifamycin SV in 100 ml of tetrahydrofurance (THF) is added 1.6 g (0.011 m) of 1-amino-4-(2-propenyl)piperazine at room temperature. After 15 minutes, tlc (CHCl₃: McOH 9:1) shows only the deep red spot of the new rifamycin derivative (Rf 0.5). The solution is concentrated to dryness. The residue is dissolved in 200 ml of ethyl acetate and washed with a buffer (pH = 4.6) to remove the excess of 1-amino-4-(2-(2-propenyl)piperazine, then with water. The organic layer is dried (Na₂SO₄) and concentrated to about 30 ml. The product crystallizes out, and, after chilling for 2 hours, is collected and dried. Yield 6.8 g (80%). M.p. 157°–159° C. The spectrophotometric data are the following:

| λ max (mμ) | ε |
|---|---|
| 470 | 13,850 |
| 333 | 24,300 |

The elementary analysis is in agreement with the theoretical values.

The starting 1-amino-4-(2-propenyl)piperazine is obtained according to the following procedure:

To a stirred suspension of 15.6 g of NaHCO₃ in 100 ml of absolute ethanol are added 11.5 g of mononitrosopiperazine and 11 g of allyl chloride and the mixture is heated at reflux. After 20 hours, the reaction mixture is filtered and concentrated, and the oily residue is dissolved in 200 ml of ethyl acetate and washed with a buffer (pH 4.5) to remove the unreacted mononitrosopiperazine. The organic layer is dried over Na₂SO₄ and concentrated under reduced pressure. The oily residue (13 g), dissolved in 50 ml of anhydrous ether, is added to a stirred suspension of 6 g of LiAlH₄ in 150 ml of anhydrous ether, and the mixture is refluxed for 2 hours. On cooling, the reaction mixture is decomposed by adding dropwise 30 ml of water and by stirring the mass for one hour at room temperature. The inorganic salts are filtered off, thoroughly washed with ether and the ether solution, after drying over Na₂SO₄, is evaporated to give an oily residue (10 g) which is distilled; b.p. 55° C/0.2 mm Hg.

EXAMPLE 2

3-[4-(2-Propynyl)-1-piperazinyl]iminomethylrifamycin SV

The title compound is obtained in a 65% yield by following the procedure of Example 1 and employing 1-amino-4-(2-propynyl)piperazine instead of 1-amino-4-(2-propenyl)piperazine. The compound, after crystallization from ethyl acetate, melts at 170° C with decomposition. The spectrophotometric data are the following:

| λ max (mμ) | ε |
|---|---|
| 470 | 13,000 |
| 333 | 23,100 |

The elementary analysis is in agreement with the theoretical values. The starting 1-amino-4-(2-propynyl)piperazine (b.p. 50°–55° C/mm Hg) is obtained according to the similar procedure followed for 1-amino-4-(2-propenyl)piperazine.

EXAMPLE 3

3-[4-(4-Pentenyl)-1-piperazinyl]iminomethylrifamycin SV

The title compound is obtained in an 85% yield from 3-formylrifamycin SV and 1-amino-4-(4-pentenyl)piperazine. M.p. 150° C with decomposition.

The spectrophotometric data are the following:

| λ max (mμ) | ε |
|---|---|
| 470 | 14,100 |
| 333 | 25,220 |

The elementary analysis is in agreement with the theoretical values.

The starting 1-amino-4-(4-pentenyl)piperazine (b.p. 79°–82° C/0.2 mm Hg) is prepared similar to the procedure followed for 1-amino-4-(2-propenyl)piperazine.

According to the procedure described above, the following rifamycin derivatives are prepared:

3-[4-(2-butenyl)-1-piperazinyl]iminomethylrifamycin SV
3-[4-(2-methyl-2-propenyl)-1-piperazinyl]iminomethylrifamycin SV
3-[4-(2-pentenyl)-1-piperazinyl]iminomethylrifamycin SV
3-[4-(1-methyl-2-butenyl)-1-piperazinyl]iminomethylrifamycin SV
3-[4-(3-methyl-2-butenyl)-1-piperazinyl]iminomethylrifamycin SV
3-[4-(4-pentynyl)-1-piperazinyl]iminomethylrifamycin SV
3-[4-(2-butynyl)-1-piperazinyl]iminomethylrifamycin SV
3-[4-(2-cyclopentenyl)-1-piperazinyl]iminomethylrifamycin SV
3-[4-(3-cyclohexenyl)-1-piperazinyl]iminomethylrifamycin SV
3-[4-(2-cyclopropylethyl)-1-piperazinyl]iminomethylrifamycin SV
3-[4-(cyclopentylmethyl)-1-piperazinyl]iminomethylrifamycin SV
3-[4-(2-cyclobutylethyl)-1-piperazinyl]iminomethylrifamycin SV
3-[4-(cycloheptylmethyl)-1-piperazinyl]iminomethylrifamycin SV
3-[4-(3-cyclopentenylmethyl)-1-piperazinyl]iminomethylrifamycin SV
3-[(4-cyclopropylmethyl)-1-piperazinyl]iminomethylrifamycin SV
3-[4-(3-butynyl)-1-piperazinyl]iminomethylrifamycin SV
3-[4-(1-methyl-3-butynyl)-1-piperazinyl]iminomethylrifamycin SV

We claim:
1. A rifamycin compound of the formula wherein Me represents a methyl group and Z represents alkenyl of 3 to 5 carbon atoms, alkynyl of 3 to 5 carbon atoms, 5- to 7-membered cycloalkenyl, cycloalkyl-($C_1$–$C_2$)alkyl wherein the cycloalkyl moiety is a 3- to 7-membered ring or cycloalkenyl-($C_1$–$C_2$)alkyl wherein the cycloalkenyl moiety is a 5- to 7-membered ring.

2. A compound as claimed in claim 1 wherein Z represents alkenyl or alkynyl of 3 to 5 carbon atoms.

3. The compound of claim 2 which is 3-[4-(2-propenyl)-1-piperazinyl]iminomethylrifamycin SV.

4. The compound of claim 2 which is 3-[4-(2-propynyl)-1-piperazinyl]iminomethylrifamycin SV.

5. The compound of claim 2 which is 3-[4-(4-pentenyl)-1-piperazinyl]iminomethylrifamycin SV.

6. A method for combatting microbial infections in mammals which comprises administering to the infected mammal once or twice a week a therapeutically effective amount of a rifamycin compound as claimed in claim 1.

7. The method of claim 6 wherein the microbial infection is provoked by a *Mycobacterium tuberculosis* strain.

8. The method of claim 6 wherein the microbial infection is provoked by the strain *Mycobacterium tuberculosis* $H_{37}R_v$.

9. A pharmaceutical composition for combatting microbial infections containing an antimicrobially effective amount of a compound of the formula wherein Me represents a methyl group and Z represents alkenyl of 3 to 5 carbon atoms, alkynyl of 3 to 5 carbon atoms, 5- to 7-membered cycloalkenyl, cycloalkyl-($3_1$–$C_2$)alkyl wherein the cycloalkyl moiety is a 3- to 7-membered ring or cycloalkenyl-($C_1$–$C_2$)alkyl wherein the cycloalkenyl moiety is a 5- to 7-membered ring, admixed with a pharmaceutical carrier.

* * * * *